United States Patent [19]

Tsuchiya et al.

[11] Patent Number: 5,346,889

[45] Date of Patent: Sep. 13, 1994

[54] PROCESS FOR EXTRACTING ENDOTOXIN

[75] Inventors: Masakazu Tsuchiya; Aya Takaoka; Kazuaki Harada, all of Amagasaki, Japan

[73] Assignee: Wako Pure Chemical Industries, Ltd., Osaka, Japan

[21] Appl. No.: 991,214

[22] Filed: Dec. 15, 1992

[30] Foreign Application Priority Data

Dec. 24, 1991 [JP] Japan ................. 3-356409

[51] Int. Cl.$^5$ .................. A61K 37/02; A61L 2/16
[52] U.S. Cl. ..................... 514/21; 530/362; 530/363; 134/42; 422/28; 422/32
[58] Field of Search ............. 514/21; 530/362, 363; 134/42; 422/28, 32

[56] References Cited

U.S. PATENT DOCUMENTS

| | | | |
|---|---|---|---|
| 3,944,391 | 3/1976 | Harris et al. | 435/18 |
| 3,959,128 | 5/1976 | Harris et al. | 128/DIG. 3 |
| 4,059,512 | 11/1977 | Harris | 128/DIG. 3 |
| 4,780,529 | 10/1988 | Hao | 530/350 |
| 4,784,989 | 11/1988 | Höök et al. | 514/21 |
| 4,834,975 | 5/1989 | Siadak et al. | 530/387 |
| 4,909,942 | 3/1990 | Sato et al. | 210/651 |

FOREIGN PATENT DOCUMENTS

WO8401108 3/1984 World Int. Prop. O. .

OTHER PUBLICATIONS

"Plasma Albumin Bibliography", 2nd edition, Research Products, Miles Laboratories, Inc. Elkhart, Indiana 46514, p. 5, 1973.

Siverhus, D. J. et al., in Surgery (St. Louis), 107(6), 1990 pp. 613–619 (Biosis BA90:52110).

Bentler et al., in Science (Wash. D.C.) 229(4716), 1985 pp. 869–871 (Biosis BA 80:96340).

Hou, Kenneth C. et al., in Biotechnol. Appl. Biochem., 12(3), 1990, pp. 315–324 (CA113(15):127889d).

Journal of Parenteral Science & Technology, vol. 40, No. 6, pp. 284–286, 1986.

Bacterial Endotoxins: Structure, Biomedical significance, and Detection with the Limulus Amebocite Lysate Test, pp. 267–280, 1985.

Journal of Parenteral Science & Technology, vol. 40, No. 6, pp. 286–291, 1991.

Journal of Parenteral Science & Technology, vol. 45, No. 2, pp. 83–87, 1991.

Primary Examiner—Michael G. Wityshyn
Assistant Examiner—C. Sayala
Attorney, Agent, or Firm—Armstrong, Westerman, Hattori, McLeland & Naughton

[57] ABSTRACT

A solution containing at least one of albumin and globulin is effective for extracting endotoxin adhered to or adsorbed on a surface of a solid such as containers, medical devices, disposable needles, etc., and thus useful as a cleaning agent for these containers, medical devices, etc.

26 Claims, 1 Drawing Sheet

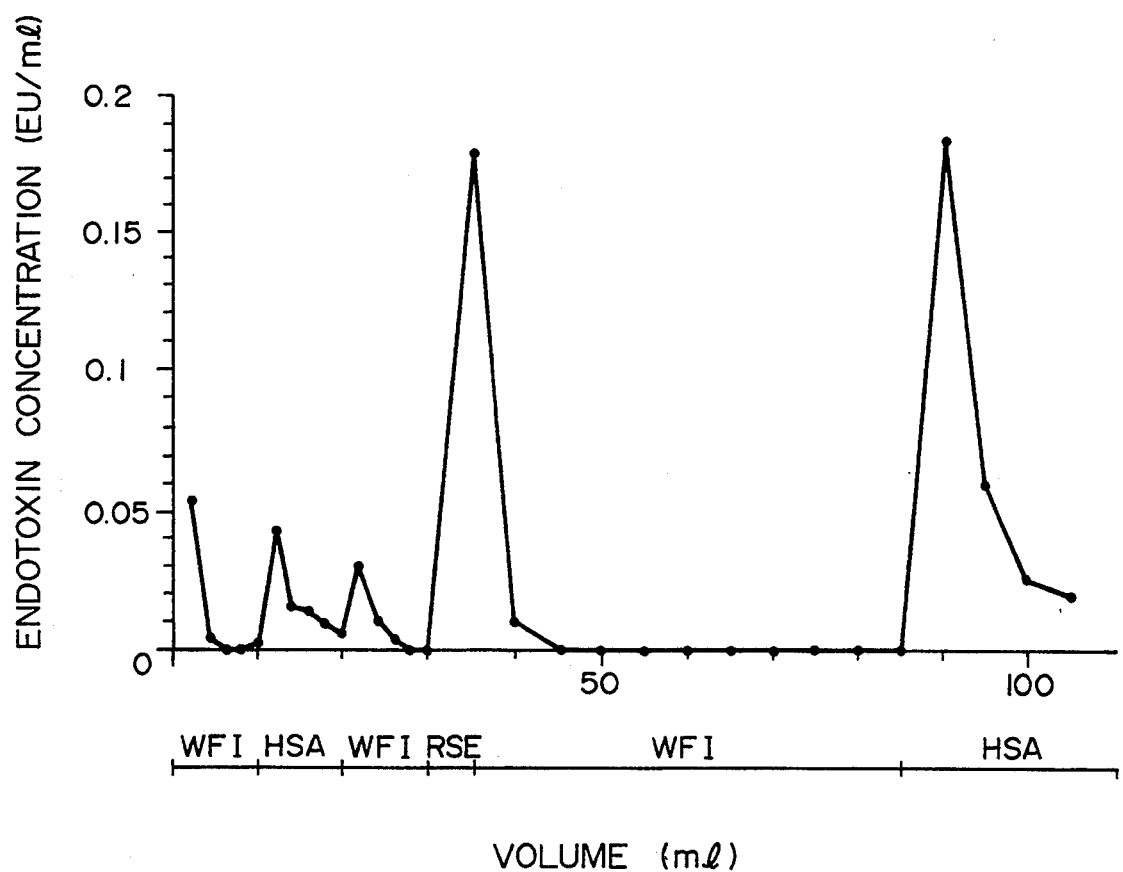

PROCESS FOR EXTRACTING ENDOTOXIN

BACKGROUND OF THE INVENTION

This invention relates to a process for extracting endotoxin adhered to or adsorbed on a surface of a solid.

Endotoxins are lipopolysaccharides present mainly in cell walls of Gram-negative bacteria and are known as pyrogens. Therefore, the measurement of endotoxin concentration in a sample is one important measurement in the fields of medical science, pharmacology and microbiology.

As to medical devices such as syringes and catheters, in order to prevent penetration of pyrogens into human bodies, it is necessary to severely control contamination due to endotoxins. Many medical devices are made from various synthetic resins, glass, metals and natural fibers. Among these materials, some are known to adsorb endotoxin thereon. In order to measure the degree of contamination of these materials with endotoxin, these materials are generally rinsed with water or a physiological saline to extract the endotoxin adhered to surfaces thereof. Then, the amount of endotoxin in the extract is measured. According to the above-mentioned method, there is a fear of not completely extracting the endotoxin adhered to or adsorbed on surfaces of solids, resulting in causing extraction of endotoxin, which has not been extracted with the water or physiological saline, when contacted with blood and drugs.

Therefore, it is earnestly desired to establish a process for extracting endotoxin from surfaces of solids effectively, and a process for measuring the degree of contamination of such materials with endotoxin precisely. At the same time, it is also earnestly desired to provide a process for effectively cleaning containers and devices contaminated with endotoxin.

SUMMARY OF THE INVENTION

It is an object of the present invention to effectively extract endotoxin which is adhered to or adsorbed on a surface of a solid and not extracted with water or a physiological saline in order to solve the above-mentioned problem.

The present invention provides a process for extracting endotoxin adhered to or adsorbed on a surface of a solid, which comprises contacting the solid with a solution containing at least one of albumin and globulin.

The present invention also provide an extracting solution for extracting endotoxin adhered to or adsorbed on a surface of a solid, comprising at least one of albumin and globulin.

The present invention further provides a cleaning process comprising cleaning a container or devices contaminated with endotoxin using a solution containing at least one of albumin and globulin.

The present invention still further provides a cleaning agent for cleaning a container or device, which comprises at least one of albumin and globulin.

BRIEF DESCRIPTION OF THE DRAWINGS

The figure is a graph showing a change of the amount of endotoxin in the filtrate obtained in Example 1.

DESCRIPTION OF THE PREFERRED EMBODIMENTS

The present inventors have earnestly studied how to extract effectively endotoxin adhered to or adsorbed on a surface of a solid and found that when a solution containing albumin and/or globulin, particularly a solution containing albumin is used, the endotoxin adhered to or adsorbed on a surface of a solid not extracted with water or a physiological saline can be extracted with extremely high efficiency. Thus, the present invention has been accomplished.

As the extracting solution containing at least one of albumin and globulin, there can be used an aqueous solution or a buffer solution containing at least one of albumin and globulin; blood plasma and serum containing as major protein components albumin and globulin.

As the blood plasma or serum, there can be used that derived from vertebrate animals, etc.

As the albumin and/or globulin, there can be used those obtained by purifying or partially purifying protein components contained in blood plasma or serum.

As the extracting solution containing albumin and/or globulin used in the present invention (hereinafter referred to as "the extracting solution"), there can be used not only those specially prepared but also those commercially available such as fresh plasma and fresh frozen human blood plasma commercially available from the Japanese Red Cross Society; therapeutic human plasma protein fraction and human serum albumin commercially available from Nihon Pharmaceutical Co., Ltd., Rorer Group Inc., Armour Biochemicals Co., Cutter Biological Co., Baxter Travenol Laboratories, Inc., The Green Cross Corp., and The Chemo-Sero-Therapeutic Research Institute; human immunoglobulin commercially available from Takeda Chemical Industries, Ltd., Otsuka Pharmaceutical Co., Ltd., The Green Cross Corp., Hoechst AG, the Japanese Red Cross Society, and Fujirebio Inc.; foetal calf serum commercially available from Whittaker Corp., Hyclone Laboratories, Inc., Gibco Laboratories.Life Technologies, Inc., and Boehringer Mannheim GmbH; and the like.

Among these solutions containing albumin and/or globulin, the most preferable one is an aqueous solution containing human serum albumin (hereinafter referred to as "HSA solution").

The amount of endotoxin extracted by the process of the present invention from a surface of a solid to which endotoxin is adhered or on which endotoxin is adsorbed, can be measured by a conventional method, for example, by a Limulus test method using a horseshoe crab hemocyte lysate (hereinafter referred to as "AL solution"). Thus, the degree of contamination of containers and devices, etc. can be measured precisely.

Needless to say, the solution containing albumin and/or globulin should not contain endotoxin in an amount which influences the results of measurement.

In order to attain such an object, it is necessary to use a solution of albumin and/or globulin selected from lots not containing endotoxin in an amount which interferes the measurement. When a solution of albumin and/or globulin containing endotoxin is used, it is necessary to remove the endotoxin using an endotoxin adsorbent or an autoclave before the measurement.

Conditions of using the autoclave are, for example, the temperature of about 121° C. for about 15 to 120 minutes, usually used.

As the endotoxin adsorbent, there can be used a carrier fixed with polymyxin B, a carrier fixed with histidine via a spacer, etc. Commercially available adsorbents are Detoxi-Gel (mfd. by PIERCE), Affi-Prep Polymyxin (mfd. by Bio-Rad Laboratories, Inc.), Pyrosep (mfd. by Tanabe Seiyaku Co., Ltd.), etc.

The concentration of the albumin and/or globulin in the extracting solution changes slightly depending on the kind of solutions used, on the difference of lots, or on the degree of adhesion or adsorption of endotoxin to or on containers, devices and the like, but is usually, in terms of the protein concentration, 0.0001 mg/ml or more. In the case of measuring the amount of endotoxin adhered to or adsorbed on surfaces of solids such as containers, devices, etc., after extraction, the concentration is preferably about 0.0001 to 6.00 mg/ml, more preferably about 0.02 to 3.00 mg/ml in terms of the protein concentration. For example, in the case of using a human serum albumin solution as the extracting solution, the concentration is usually 0.0001% w/v or more, preferably about 0.0001 to 0.5% w/v (protein content: about 0.001 to 6.00 mg/ml) particularly in the case of measuring the endotoxin amount after extraction, more preferably about 0.002 to 0.25% w/v (protein content: about 0.02 to 3.00 mg/ml). In the case of using a human plasma solution as the extracting solution, the concentration is, in terms of protein concentration, 0.0001 mg/ml or more, preferably about 0.0001 to 1.0 mg/ml particularly in the case of measuring the endotoxin amount after extraction, more preferably about 0.1 to 0.5 mg/ml.

When the extract obtained by the extracting method is subjected to the so-called Limulus test using an AL solution for measuring an endotoxin concentration, it is desirable to obtain precise measured value without any troubles.

As the extracting solution, there can be used a human serum albumin (HSA) solution, a human plasma solution, a human serum solution, a fetal bovine serum solution, a calf serum albumin (BSA) solution, a globulin solution, etc. When the protein concentration in these extracting solution becomes higher, an inhibition takes place in the measurement of endotoxin by the Limulus test after the extraction, resulting in giving lower values than the true values. Therefore, in the case of measuring the amount of endotoxin adhered to or adsorbed on surfaces of solids such as containers and devices, the use of a solution having a higher protein concentration is not preferable. The above-mentioned preferable concentration range of the albumin and/or globulin solution, particularly the upper limit, is determined by considering the above-mentioned fact. When the albumin and/or globulin solution is used only for cleaning or extraction, there is no problem of using a solution having a higher protein concentration. The concentration of the extracting solution causing interference at the time of measurement by the Limulus test remarkably changes depending on the kind of the extracting solutions used. In the case of the HSA solution, such an interference takes place at the protein concentration of about 6.0 mg/ml. In the case of the human plasma, such an interference takes place at the protein concentration of about 1 mg/ml.

As the AL solution used for measuring the amount of endotoxin in the extracted solution obtained by the extracting process of the present invention by the Limulus test, there can be used those extracted from hemocytes of horseshoe crab belonging to Limulus genus, Tachypleus genus or Carcinoscorpius genus and react with endotoxin or $\beta$-1,3-glucan to undergo coagulation reaction. It is, of course, possible to use an AL solution prepared from freeze-dried products of AL solutions which are commercially available from, for example, Associates of Cape Cod Inc. (ACC), Whittaker Bioproducts, Inc., Endosafe Inc., Seikagaku Corp., Wako Pure Chemical Industries, Ltd., etc.

As the Limulus test for measuring the amount of endotoxin in the extract obtained by the extracting process of the present invention, there can be used those conventionally used. For example, a Gel-clot technique, a chromogenic technique, an kinetic-turbidimetric technique, etc., described in, e.g. FDA Guide Line (guide line on validation of the Limulus amoebocyte lysate test as an end-product endotoxin test for human and animal parenteral drugs, biological products, and medical devices, Food and Drug Adm. (1987)).

When the extracting solution of the present invention is used, endotoxin adhered to or adsorbed on a surface of a solid can be extracted effectively. Therefore, the extracting solution of the present invention can be used as a cleaning agent for cleaning containers and devices, etc. contaminated with endotoxin.

As the containers and devices, etc. to be cleaned using the extracting solution, there are exemplified medical devices such as disposable needles, disposable syringes, disposable blood administration sets, disposable infusion sets, disposable blood collecting devices, disposable sets for pump oxygenerator, artificial blood vessels for medical use, artificial cardiac valves, heart pace makers, hemodialyzers, as well as disposable experimental equipments used in the endotoxin determination (sterilized pipets, sterile test tubes, sterile pipet chips, etc.).

The present invention is explained in detail referring to the following Examples, in which all percents are by weight unless otherwise specified.

EXAMPLE 1

Reagents (1) Endotoxin solution

*E. coli* reference endotoxin (standard endotoxin specified by the Japanese Pharmacopoeia, lipopoly-saccharide derived from *E. coli* UKT-B strain, containing endotoxin corresponding to 16000 EU per vial) optionally diluted with water for injection was used.

(2) AL solution

Limulus ES-Test Wako (mfd. by Wako Pure Chemical Industries, Ltd.)

(3) HSA solution

25% HSA solution (mfd. by Cutter Biological, for injection) was diluted with water for injection to 1% and autoclaved at 121° C. for 20 minutes. The solution was confirmed not to contain any detectable endotoxin before use.

Procedures

Using a Minisarts NML (mfd. by Sartrius) which is a filtration unit for syringe with a cellulose acetate filter, 10 ml of water for injection was filtered. Then, 10 ml of 1% HSA solution was filtered, followed by filtration of 10 ml of water for injection to rinse the HSA away from the filter. The resulting filtrates were fractionated in amounts of 2 ml, respectively. Using the Minisarts after pre-cleaning, 5 ml of an endotoxin solution (1.0 EU/ml) was filtered to adsorb endotoxin on the filter. Subsequently, 50 ml of water for injection and 25 ml of 1% HSA solution were filtered in this order. The filtrates were fractionated in amounts of 5 ml, respectively. The concentration of endotoxin in the fractionated filtrates was measured using a Toxinometer ET-201 (mfd. by Wako Pure Chemical Industries, Ltd.). The measuring procedures were as follows.

To 0.1 ml of the AL solution, 0.1 ml of a sample was added and vortexed. Then, the time required for reducing the transmittance through the above mixed solution to 5% (hereinafter referred to as "Tg") was measured at 37° C. On the other hand, endotoxin solutions having various concentrations prepared by using water for injection and the endotoxin solution as samples were subjected to the same measurement as mentioned above to prepare a calibration curve showing a relationship between the endotoxin concentration and Tg.

Based on the calibration curve, the endotoxin concentration in the sample was calculated.

Results

The results are shown in FIG. 1 which shows a change of endotoxin amounts in the filtrates.

In FIG. 1, WFI means water for injection, HSA means the 1% human serum albumin solution, and RSE is the endotoxin solution (1.0 EU/ml).

In the filtration of water for injection, a small amount of endotoxin was detected in the filtrate of initial stage. With the continuation of the filtration of the distilled water for injection, no endotoxin was detected in the filtrate. When the 1% HSA solution was filtered under this state, endotoxin was detected in the filtrate. The results show that endotoxin was originally adhered to or adsorbed on the Minisarts, said endotoxin being not extracted with the water for injection but extracted with the 1% HSA solution.

After this, when water for injection was filtered again, endotoxin was detected again in the filtrate. This seems to be that the endotoxin adhered to or adsorbed on the Minisarts filter and insoluble in the water for injection is changed to be soluble by the HSA solution, and to be released from the filter surface into the water for injection.

Then, the endotoxin solution was filtered and after that, the water for injection was filtered. After detectable endotoxin was diminished in the filtrate, the 1% HSA solution was filtered, then a large amount of endotoxin was detected. These results show that when the endotoxin solution was filtered with the Minisarts, a part of endotoxin adheres to or adsorbs on the filter and not extracted with the water for injection sufficiently, but can be extracted with the 1% HSA solution.

As is clear from the above results, the endotoxin which is adhered to or adsorbed on the surface of solid and cannot be extracted with the distilled water for injection, can be extracted with the 1% HSA solution.

EXAMPLE 2

Reagents (1) Endotoxin solution
The same as that used in Example 1.
(2) AL solution
The same as that used in Example 1.
(3) HSA solution
The same as that used in Example 1.
(4) NaCl solution
A physiological saline for injection (mfd. by Otsuka Pharmaceutical Co., Ltd.)
(5) Plasmanate solution Plasmanate (mfd. by Cutter Biological, therapeutic human plasma) was diluted with water for injection 10 times and autoclaved at 121° C. for 20 minutes.

(6) Sodium deoxycholate (DOC) solution
DOC (mfd. by Wako Pure Chemical Industries, Ltd., for biochemistry) was dissolved in water for injection to prepare a 1% solution. The 1% solution was autoclaved at 121° C. for 20 minutes, followed by dilution to 0.01%.

(7) Sodium dodecylsulfate (SDS) solution
SDS (mfd. by Wako Pure Chemical Industries, Ltd., for biochemistry) was dissolved in water for injection to prepare a 1% solution. The 1% solution was autoclaved at 121° C. for 20 minutes, followed by dilution to 0.01%.

The reagents (3) to (7) were used after confirmation of no detectable endotoxin.

Procedures

After cleaning a Minisarts NML with 2 ml of 1% HSA solution and 20 ml of water for injection, 5 ml of endotoxin solution (1.0 EU/ml) was filtered. Then, using water for injection, filtration was carried out until no endotoxin was detected in the filtrate. Then, using each 3 ml of the HSA solution, the NaCl solution, the Plasmanate solution, the DOC solution, or the SDS solution, as an extracting solution, filtration was carried out. The endotoxin concentration in each filtrate of extracting solution was measured in the same manner as described in Example 1.

Results

The amount of endotoxin in each filtrate of extracting solution was shown in Table 1. As is clear from Table 1, endotoxin is detected in all the filtrates of extracting solutions, but the detected amount of endotoxin is particularly large in the HSA solution and the Plasmanate solution.

From the results mentioned above, it is clear that the HSA solution and the Plasmanate solution belonging to the present invention are particularly excellent in extracting ability among various endotoxin extracting solutions.

TABLE 1

| Extracting solution | Endotoxin concentration (%)* |
|---|---|
| HSA solution | 68.7 |
| NaCl solution | 16.8 |
| Plasmanate solution | 39.5 |
| DOC solution | 11.1 |
| SDS solution | 18.4 |

Note
*The amount of endotoxin adhered to or adsorbed on the filter (a value obtained by subtracting the endotoxin amount in the endotoxin solution after filtration from the endotoxin amount in the endotoxin solution after filtration) was taken as 100% for the calculation.

EXAMPLE 3

Reagents (1) Endotoxin solution
The same as that used in Example 1.
(2) AL solution
The same as that used in Example 1.
(3) HSA solution
2% solution of HSA prepared in the same manner as described in Example 1.

PROCEDURES

Sterile serum tubes made from polypropylene (mfd. by Corning Glass Works, 2 ml in volume) in number of ten, were charged with 1.0 ml of water for injection, respectively. After shaking, 0.2 ml of the solution was taken out for use as an extracted sample using water for injection as an extracting solution. To each serum tube, 0.8 ml of 2% HSA solution was added and shaken to give an extracted sample using 1% HSA solution. The endotoxin concentration in each extracted sample was measured in the same manner as described in Example 1.

Results

The endotoxin amount in each extracted sample was shown in Table 2.

As is clear from Table 2, endotoxin is not extracted with the water for injection, or even if extracted in a small amount, but when the HSA solution is used, endotoxin is extracted in a considerably large amount.

TABLE 2

| Serum tube No. | Extracted sample | |
|---|---|---|
| | Water for injection (EU/ml) | HSA solution (EU/ml) |
| 1 | Not detected | Not detected |
| 2 | Not detected | 0.015 |
| 3 | 0.004 | 0.013 |
| 4 | Not detected | 0.005 |
| 5 | " | 0.003 |
| 6 | " | Not detected |
| 7 | 0.010 | 0.027 |
| 8 | 0.006 | 0.073 |
| 9 | Not detected | 0.004 |
| 10 | Not detected | Not detected |

EXAMPLE 4

Reagents (1) Endotoxin solution
The same as that used in Example 1.
(2) AL solution
The same as that used in Example 1.
(3) HSA solution
The same as that used in Example 2

Procedures

To a glass test tube containing 6 disposable needles (mfd. by Japan Medical Supply Co., size 22 G), 10 ml of endotoxin solution (0.1 EU/ml) and 10 ml of 1% HSA solution containing 0.1 EU/ml and endotoxin were added and mixed to measure the endotoxin amounts in individual solutions in the same manner as described in Example 1.

As negative controls, those containing no disposable needles were measured, respectively. Taking the resulting value as 100%, the recovery of endotoxin in the case of placing the disposable needles was obtained.

Results

The recovery of endotoxin in each solution is shown in Table 3. When the HSA solution was not co-present, the recovery of endotoxin was lowered to as large as 10% by the presence of the disposable needles. But when the HSA solution was co-present, almost no influence of the disposable needles was admitted.

As is clear from the above results, the HSA solution is effective for extracting endotoxin from disposable needles.

TABLE 3

| Sample | Recovery of endotoxin (%) |
|---|---|
| HSA solution containing endotoxin | 86 |
| Aqueous solution of endotoxin | 10 |

EXAMPLE 5

Reagents (1) Endotoxin solution
The same as that used in Example 1.
(2) AL solution
A Limulus amoebocyte lysate (mfd. by Wako Pure Chemical Industries, Ltd., labeled sensitivity: 0.25 EU/ml, for 5 ml) was reconstituted with 5 ml of buffer solution for reconstitution of Limulus ES Test Wako (mfd. by Wako Pure Chemical Industries, Ltd.), and used as an AL solution.
(3) Globulin solution
Human immunoglobulin for injection ($\gamma$-globulin-NICHIYAKU, Co., containing 15% IgG) was diluted to 0.5% and heated at 65° C. for 20 minutes. The immunoglobulin for injection was selected from a lot free from detectable endotoxin.

Procedures

Endotoxin was adhered to or adsorbed on a Minisarts NML in the same manner as described in Example 1. After filtering water for injection until no endotoxin was detected in the resulting filtrate, 5 ml of 0.5% globulin solution was filtered. The endotoxin amount in the filtrate was measured using a Toxinometer ET-201 (mfd. by Wako Pure Chemical Industries, Ltd.) in the same manner as described in Example 1.

Results

The endotoxin concentrations of globulin filtrates are shown in Table 4.

As is clear from Table 4, some endotoxin adhered to or adsorbed on the Minisarts is not extracted with water for injection, but is extracted with the globulin solution. Thus, the globulin solution is effective for extracting endotoxin.

TABLE 4

| Minisarts No. | Endotoxin concentration in globulin filtrate (EU/ml) |
|---|---|
| 1 | 0.12 |
| 2 | 0.09 |
| 3 | 0.10 |

EXAMPLE 6

Reagents (1) Endotoxin solution
The same as that used in Example 1
(2) AL solution
A Limulus amoebocyte lysate (mfd. by Wako Pure Chemical Industries, Ltd., gelation sensitivity: 0.06 EU/ml) was reconstituted with 2.0 ml of water and used as an AL solution.

(3) HSA solution

25% HSA solution (mfd. by Cutter Biological, for injection) was diluted with water for injection to 1% and autoclaved at 121° C. for 20 minutes. The solution was confirmed not to contain any detectable endotoxin before use.

(4) Fetal bovine serum

Fetal bovine serum (mfd. by Whittaker Bioproduct, Inc.) in an amount of 50 ml was diluted with water 10 times, and heated at 100° C. for 10 minutes on a water bath.

(5) Human plasma

Human pooled plasma was diluted with water for injection 10 times, and heated at 100° C. for 10 minutes on a water bath.

(6) Globulin solution

γ-Globulin (bovine cohn fraction 11,111) in an amount of 5 g was adjusted to 0.2%, autoclaved at 120° C. for 20 minutes, and diluted with endotoxin-free water to 0.1%.

Procedures

Each disposable sterile polypropylene tubes (Fakon 2059) was spiked with 2.0 μl of endotoxin solution (25 EU/ml containing 6.25% ethanol) and dried overnight (15 hours) at room temperature. The tubes were used as the endotoxin challenged tubes.

Test samples (HSA solution, fetal bovine serum solution, human plasma solution, globulin solution) were diluted to suitable concentrations, and added to the endotoxin challenged tubes in an amount of 1 ml each to conduct extraction for 1 hour with frequent stirring. The endotoxin concentration in each extracting solution was measured in the same manner as described in Example 1.

Results

Endotoxin recovery in each solution is shown in Table 5.

As is clear from Table 5, when the protein concentration is made the same (1.20 mg/ml), the recovery (%) of endotoxin is 109%, 71% and 57%, respectively, in the case of using 0.1% HSA solution, 32.5 times-diluted fetal bovine serum albumin and 60.8 times-diluted human plasma in this order. This shows that the 0.1% HSA solution is the most effective for extracting endotoxin at this protein concentration. Further, in the case of making the albumin content the same (1.20 mg/ml), the 0.1% HSA solution, 22.8 times-diluted fetal bovine serum albumin and 42.6 times-diluted human blood plasma show the endotoxin recovery of 109%, 59% and 54%, respectively. This means that the bovine serum and the human blood plasma show lower values than the HSA solution at this albumin concentration. In addition, in the case of comparison of the HSA solution with the globulin solution, the endotoxin recovery is 106% when 0.0096% HSA solution (protein concentration: 0.115 mg/ml) is used, while the endotoxin recovery is 51% when 0.1% globulin solution (protein concentration: 0.115 mg/ml) is used. This also shows that the HSA solution is more effective than the globulin solution at this protein concentration.

TABLE 5

| Extracting solution | Protein concentration (mg/ml) | Albumin concentration (mg/ml) | Endotoxin recovery (%) (mean of 5 replicate) |
|---|---|---|---|
| Endotoxin-free water | — | — | 34 |
| 0.0096% HSA soln. | 0.115 | 0.115 | 106 |
| 0.1% HSA soln. | 1.20 | 1.20 | 109 |
| 22.8 times-diluted fetal bovine serum | 1.71 | 1.20 | 59 |
| 32.5 times-diluted fetal bovine serum | 1.20 | 0.84 | 71 |
| 42.6 times-diluted human blood plasma | 1.71 | 1.20 | 54 |
| 60.8 times-diluted human blood plasma | 1.20 | 0.84 | 57 |
| 0.1% globulin soln. | 0.115 | — | 51 |

EXAMPLE 7

Concentrations of HSA solutions

Reagents (1) Endotoxin solution
The same as that used in Example 1
(2) AL solution
The same as that used in Example 6
(3) HSA solution
The 25% HSA solution (mfd. by Cutter Biological, for injection) was diluted with distilled water for injection to 1% and autoclaved at 121° C. for 20 minutes. The solution was confirmed not to contain any detectable endotoxin before use. Then, the resulting solution was diluted with endotoxin-free water.

Procedures

The same as Example 6.

Results

Table 6 shows endotoxin recovery by the HSA solutions having a variety of concentrations.

As is clear from Table 6, the HSA solution is effective for extracting endotoxin even in a concentration of as low as about 0.0001%. On the other hand, with an increase of the HSA concentration, the endotoxin recovery seems to be lowered at a sight. But, this is caused by the above-mentioned inhibition of the HSA solution having a higher protein concentration at the measurement of endotoxin by the Limulus test. This does not mean that the extracting ability is lowered.

TABLE 6

| Extracting solution | Protein (mg/ml) | Endotoxin recovery (%) (mean of 5 replicate) |
|---|---|---|
| Endotoxin-free water | — | 47 |
| 0.0001% HSA solution | 0.0012 | 60 |
| 0.001% HSA solution | 0.012 | 70 |
| 0.002% HSA solution | 0.024 | 85 |
| 0.0039% HSA solution | 0.047 | 108 |
| 0.0078% HSA solution | 0.094 | 105 |
| 0.0156% HSA solution | 0.187 | 107 |
| 0.0313% HSA solution | 0.374 | 105 |
| 0.0625% HSA solution | 0.749 | 97 |
| 0.125% HSA solution | 1.50 | 99 |
| 0.25% HSA solution | 3.00 | 84 |
| 0.5% HSA solution | 6.00 | 72 |
| 1.0% HSA solution | 12.00 | 54 |

EXAMPLE 8

Concentration of human plasma solution

Reagents (1) Endotoxin solution
The same as that used in Example 1.
(2) AL solution
The same as that used in Example 6
(3) Human plasma solution
Human pooled plasma was diluted with endotoxin-free water 10 times, heat treated at 100° C. for 10 minutes on a water bath, and diluted with endotoxin-free water.

Procedures

The same as Example 6.

Results

Table 7 shows endotoxin recovery by the human plasma solutions having a variety of concentrations.

As is clear from Table 7, the human plasma solution is the most effective for extracting endotoxin at the concentration obtained by dilution of 320 times. With a decrease of the concentration, the endotoxin extracting ability is lowered gradually. Since the inhibition also takes place in the case of the human plasma solution having the higher protein concentration at the measurement of endotoxin in the extract, the recovery value is lowered as shown in Table 7. But this does not mean the lowering of extracting ability of endotoxin.

TABLE 7

| Extracting solution | Protein (mg/ml) | Endotoxin recovery (%) (Mean of quadraplicate) |
| --- | --- | --- |
| Endotoxin-free water | — | 39 |
| Human plasma solution (dilution) 10240 times | 0.008 | 70 |
| 5960 times | 0.015 | 70 |
| 2560 times | 0.031 | 74 |
| 1280 times | 0.062 | 82 |
| 640 times | 0.123 | 87 |
| 320 times | 0.247 | 94 |
| 160 times | 0.493 | 81 |
| 80 times | 0.988 | 62 |
| 40 times | 1.975 | 50 |
| 20 times | 3.95 | 42 |
| 10 times | 7.90 | 30 |

As mentioned above, according to the present invention, endotoxin adhered to or adsorbed on surfaces of solids such as containers, devices, etc., can effectively extracted. Further, according to the present invention, the endotoxin which is difficultly or hardly extracted by conventional extracting methods, can easily and effectively extracted.

What is claimed is:

1. A process for extracting endotoxin adhered to or adsorbed on a surface of a container or device, which comprises contacting the container or device with a solution comprising at least one of albumin and globulin.

2. A process according to claim 1, wherein the solution comprises albumin.

3. A process according to claim 2, wherein the albumin is human serum albumin.

4. A process according to claim 3, wherein the human serum albumin is contained in an amount of 0.0001 to 0.5% w/v.

5. A process according to claim 2, wherein the solution comprising albumin is a plasma solution or serum solution.

6. A process according to claim 1, wherein at least one of albumin and globulin is contained in the solution in a concentration of 0.0001 to 6 mg/ml in terms of protein concentration.

7. A process according to claim 1, wherein the albumin and globulin are previously autoclaved to remove endotoxins.

8. A solution for extracting endotoxin adhered to or adsorbed on a surface of a solid, which comprises an endotoxin-free water or buffer solution and at least one of albumin and globulin in a concentration of 0.0001 to 6 mg/ml in terms of protein concentration.

9. A solution according to claim 8, which contains albumin.

10. A solution according to claim 9, which contains albumin is human serum albumin.

11. A solution according to claim 10, which contains human serum albumin is contained in an amount of 0.0001 to 0.5% w/v.

12. A solution according to claim 9, which contains solution containing albumin is a plasma solution or a serum solution.

13. A solution according to claim 8, wherein the albumin and globulin are previously autoclaved to remove endotoxins.

14. A process for cleaning containers or devices contaminated with endotoxin, which comprises rinsing the containers or devices using a solution comprising at least one of albumin and globulin.

15. A process according to claim 14, wherein the solution contains albumin.

16. A process according to claim 15, wherein the albumin is human serum albumin.

17. A process according to claim 16, wherein the human serum albumin is used in an amount of 0.0001 to 0.5% w/v.

18. A process according to claim 15, wherein the solution containing albumin is a plasma solution or serum solution.

19. A process according to claim 14, wherein at least one of albumin and globulin is contained in the solution in a concentration of 0.0001 to 6 mg/ml in terms of protein concentration.

20. A process according to claim 14, wherein the albumin and globulin are previously autoclaved to remove endotoxins.

21. A cleaning agent for cleaning containers or devices contaminated with endotoxin, which comprises an endotoxin-free water or buffer solution and at least one of albumin and globulin in a concentration of 0.0001 to 6 mg/ml in terms of protein concentration.

22. A cleaning agent according to claim 21, which is a solution containing albumin.

23. A cleaning agent according to claim 22, wherein the albumin is human serum albumin.

24. A cleaning agent according to claim 23, wherein the human serum albumin is used in an amount of 0.0001 to 0.5% w/v.

25. A cleaning agent according to claim 22, wherein the solution containing albumin is a plasma solution or serum solution.

26. A cleaning agent according to claim 21, wherein the albumin and globulin are previously autoclaved to remove endotoxins.

* * * * *